(12) United States Patent
Markowitz et al.

(10) Patent No.: US 8,652,853 B2
(45) Date of Patent: Feb. 18, 2014

(54) HYBRID PRECONCENTRATOR FOR DETECTION OF MATERIALS

(75) Inventors: Michael A Markowitz, Springfield, VA (US); Mazyar Zeinali, Columbia, MD (US); R Andrew McGill, Lorton, VA (US); Anne W Kusterbeck, Annandale, VA (US); Jennifer L Stepnowski, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1055 days.

(21) Appl. No.: 12/246,573

(22) Filed: Oct. 7, 2008

(65) Prior Publication Data

US 2010/0083736 A1 Apr. 8, 2010

(51) Int. Cl.
*G01N 33/543* (2006.01)

(52) U.S. Cl.
USPC ........................................................ 436/518

(58) Field of Classification Search
USPC .................................................. 436/815, 518
See application file for complete search history.

(56) References Cited

U.S. PATENT DOCUMENTS

| | | |
|---|---|---|
| 6,171,378 B1 | 1/2001 | Manginell et al. |
| 6,310,110 B1 | 10/2001 | Markowitz et al. |
| 6,583,191 B2 | 6/2003 | Markowitz et al. |
| 6,660,780 B2 | 12/2003 | Markowitz et al. |
| 6,673,246 B2 | 1/2004 | Markowitz et al. |
| 6,713,416 B2 | 3/2004 | Markowitz et al. |
| 6,902,701 B1 | 6/2005 | Hughes et al. |
| 7,705,062 B2 * | 4/2010 | Markowitz et al. ............. 521/99 |
| 2003/0139483 A1 | 7/2003 | Markowitz et al. |
| 2004/0126814 A1 | 7/2004 | Singh et al. |
| 2005/0095722 A1 | 5/2005 | McGill et al. |
| 2005/0226778 A1 | 10/2005 | Houser et al. |
| 2005/0227258 A1 * | 10/2005 | Bright ............................... 435/6 |
| 2007/0054418 A1 | 3/2007 | Markowitz et al. |

FOREIGN PATENT DOCUMENTS

| | | |
|---|---|---|
| WO | 2005001426 | 1/2005 |
| WO | 2005029030 | 3/2005 |

OTHER PUBLICATIONS

Markowitz et al., "Effects of Added Organosilanes on the Formation and Adsorption Properties of Silicates Surface-Imprinted with an Organophosphonate" Langmuir, 16, 6148-6155 (2000).

Markowitz et al., "Influence of Quaternary Amine Organosilane Structure on the Formation and Adsorption Properties of Surface-Imprinted Silicates" Langmuir, 17, 7085-7092 (2001).

Martin et al., "Microfabricated vapor preconcentrator for portable ion mobility spectroscopy" Sensors and Actuators B, 126, 447-454 (2007).

(Continued)

*Primary Examiner* — Lore Jarrett
(74) *Attorney, Agent, or Firm* — US Naval Research Laboratory; Joseph T. Grunkemeyer

(57) ABSTRACT

A device having: one or more substrates in an enclosure having an inlet and an outlet; a template directed molecular imprinted material on the substrates; and a heater to heat the material. A method of: providing the above device including a sensor coupled to the outlet; flowing a gas though the device; heating the material; and flowing any vapor evolved from the material into the sensor.

24 Claims, 2 Drawing Sheets

(56) References Cited

OTHER PUBLICATIONS

Pai et al., "Towards Enhanced Detection of Chemical Agents: Design and Development of a Microfabricated Preconcentrator" Transducers & Eurosensors '07: The 14th International Conference on Solid-State Sensors, Actuators and Microsystems, 2291-2294 (Lyon, France, Jun. 10-14, 2007).

Trammell et al., "Nanoporous Organosilicas as Preconcentration Materials for the Electrochemical Detection of Trinitrotoluene" Anal. Chem., 80, 44627-4633 (2008).

U.S. Appl. No. 60/477,032, filed Jun. 10, 2003, "Cascade avalanche sorbent plate array (CASPAR)".

U.S. Appl. No. 60/708,913, filed Aug. 17, 2005, "Fluorphore embedded/incorporating/bridged molecularly imprinted periodic mesporous organosilicas (PMOs) as recognition elements for optical sensors".

U.S. Appl. No. 60/826,421, filed Sep. 21, 2006, "Optically Clear Monolith With Embedded Molecularly Imprinted Mesoporous Organosilicas".

U.S. Appl. No. 11/465,343, filed Aug. 17, 2006, "Fluorophore Embedded/Incorporating/Bridged Periodic Mesoporous Organosilicas As Recognition Elements for Optical Sensors".

Search Report and Written Opinion in PCT/US2009/059791.

Taranekar et al., "Pinacolyl methyl phosphonate (PMP) detection by molecularly imprinted polymers (MIP): A labile covalent bonding approach." Polymer 47, 6485-6190 (2006).

* cited by examiner

HYBRID PRECONCENTRATOR FOR DETECTION OF MATERIALS

TECHNICAL FIELD

The subject matter is generally related to sensor preconcentrators.

DESCRIPTION OF RELATED ART

Many sensors exist that can detect volatile organic compounds (VOCs), nerve agents, and explosives if positioned within a few centimeters of the source. The sensitivity of sensors to detect specific analytes is proportional to the concentration of the target analyte. Preconcentration allows the collection of enough sample mass to obtain detectable signals from a sensor array. Preconcentrators have been used in analytical chemistry applications for collecting analytes that are present in very low concentrations in air or water. It is advantageous for a sensor preconcentrator to have enough selectivity to bias adsorption in favor of the target analytes. For instance, a preconcentrator for an explosives sensor may preferentially adsorb aromatics and nitroamines from complex mixtures and contaminated environments. To achieve the goal of efficient preconcentration, the preconcentrator also may have high adsorption capacity and rapid adsorption/desorption kinetics. Many sorbents were developed to act as adsorbers of molecules and as sensor preconcentrators. One drawback of existing materials is the low rate of analyte desorption from most of these sorbents (Davis et. al., Sensors and Actuators B. 2005, 104, 207). (All publications and patent documents referenced throughout this application are incorporated herein by reference.) Other sorbents have relatively low adsorption capacities although they meet a number of the criteria for use as preconcentrators (Lu et. al, Anal. Chem., 2001, 73, 3449-3457). Because of these less-than-optimal features of currently available adsorbent resins, portable systems for doing quantitative analysis of multianalyte, low concentration air samples (in industrial hygiene for example), are fairly complicated.

Template directed molecular imprinting (TDMI) is a process to engineer selectively adsorbing robust organosilicas with rapid adsorption-desorption kinetics helpful for effective preconcentration, sensitivity, stability, resistance to fouling, and adsorption capacities much greater than those of other sorbents. The ability to fabricate these materials as powders, thin films, and monoliths makes them suitable for in use in any sensor configuration. TDMI is a surface imprinting process that involves introducing a surface active molecule with a structure similar to that of the targeted analyte during synthesis of the organosilica sorbent. A mixture of this imprint molecule and a micelle-forming surfactant self-assemble into a microstructure that acts as a template for the formation of a porous organosilica. Using established template-directed synthetic methods, this microstructure would be mineralized. During mineralization, the imprint molecule is in contact with the surface of the metal oxide structure as it forms, creating a negative image or "imprint" of the shape of the imprint molecule in the new material's surface. After the surfactant is washed away, a robust material containing molecular recognition sites in its surfaces remains. Solid-state NMR analysis has demonstrated that the TDMI process effects a reorganization of the surface adsorption sites from a heterogeneous to homogeneous population. This leads to a sharp increase in adsorption capacity as well as imparting selectivity for the sorbate.

The cascade sorbent plate array (CASPAR) preconcentrator is a series of stacked thin membrane hotplates, each with a coating of sorbent material. Air flows through holes in the room temperature preconcentrator while analyte is selectively sorbed to the chemoselective material. CASPAR is then heated, in a few hundred microseconds, sending a narrow pulse of analyte into the detector. The preconcentrator has been shown to enhance selectivity and sensitivity.

BRIEF SUMMARY

Disclosed herein is a device comprising: one or more substrates in an enclosure; a template directed molecular imprinted material on the substrates; an inlet and an outlet of the enclosure that permit air flow through the enclosure and over the substrates; and a heater that permits heating the template directed molecular imprinted material.

Also disclosed herein is a method comprising: providing the above device including a sensor coupled to the outlet for detecting vapors; flowing a gas though the device during a sampling period; heating the template directed molecular imprinted material with the heater after the sampling period; and flowing any vapor evolved from the template directed molecular imprinted material during the heating into the sensor.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
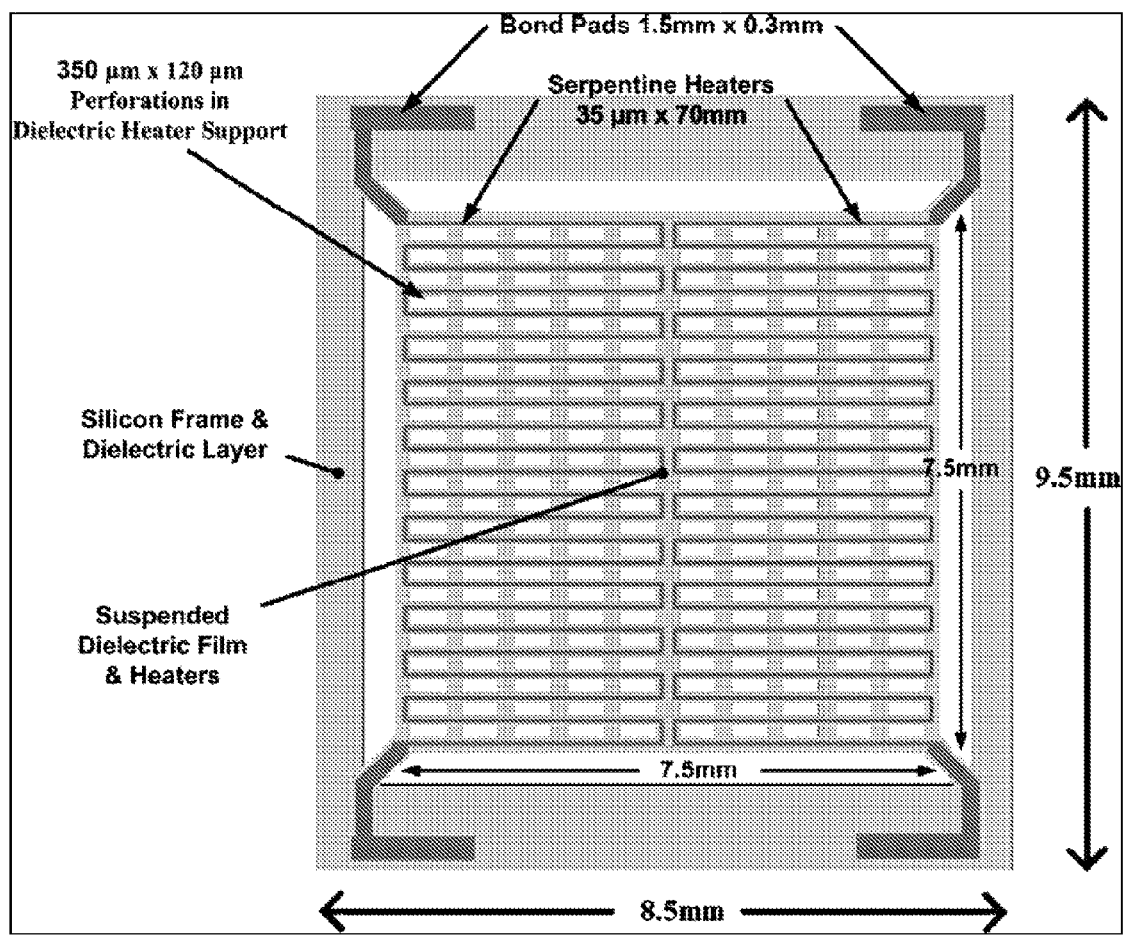
FIG. 1 shows an example CASPAR preconcentrator.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Described herein is the preparation and use of a nanoporous organosilica sorbent coated MEMs (microelectronic mechanical) device for rapid pre-concentration and desorption placed in-line with an ion mobility spectrometer (IMS) sensor for high throughput trace and remote detection of volatile organic chemicals (VOCs) and illicit materials such as nerve agents and TNT. The pre-concentration sorbent is a highly selective adsorbing organic-inorganic hybrid polymer with high surface area and porosity. The nanoporous organosilica sorbent coated MEMs preconcentrator may be a series of stacked thin membrane hotplates, such as a CASPAR, each with a coating of sorbent material. (The CASPAR preconcentrator is described in detail by Houser et al., US Patent Application Publication No. 2005/0226778; McGill et al., US Patent Application Publication No. 2005/0095722; Houser et al., U.S. Provisional Patent Application No. 60/477,032; Pai et al., "Towards Enhanced Detection of Chemical Agents: Design and Development of a Microfabricated Preconcentrator" Transducers & Eurosensors '07: The 14th International Conference on Solid-State Sensors, Actuators and Microsystems, 2291-2294 (Lyon, France, Jun. 10-14, 2007); and Martin et al., "Microfabricated vapor preconcentrator for portable ion mobility spectroscopy" *Sensors and Actuators B,* 126, 447-454 (2007).) Air flows through holes in the room temperature preconcentrator while analyte is selectively sorbed to the chemoselective material. The MEMs device is then heated, in a few hundred microseconds, sending a narrow pulse of analyte into the detector. Silica-based organic-inorganic hybrid materials can easily be incorporated onto this MEMs device. Because this sorbent is easily regenerated, desorption is rapid thereby enabling fast sensor response times.

The hybrid preconcentrator may be a robust material that selectively collects, concentrates, retains, and detects analytes such as explosives with improved sensor response times and limits of detection in complex environments, and provides at least a 3 fold improvement in preconcentration/sensitivity. Selective and efficient preconcentration methods would impact all sensor technology and offers the potential for an ultra-sensitive sensor suite with millisecond to seconds response time for the detection of explosives, chemical agents and other targeted molecules in field-deployable instruments such as UAVs (unmanned aerial vehicles), UUVs (unmanned underwater vehicles), and hand held detection devices for first responders. Alternatively, these sorbents could be used as passive collector materials for "leave behind" patch styled trapping system.

Template directed molecular imprinted materials are described in detail by Markowitz et al., U.S. Pat. Nos. 6,310,110; 6,583,191; 6,660,780; 6,673,246; 6,713,416; Markowitz et al., "Influence of Quaternary Amine Organosilane Structure on the Formation and Adsorption Properties of Surface-Imprinted Silicates" *Langmuir,* 17, 7085-7092 (2001); and Markowitz et al., "Effects of Added Organosilanes on the Formation and Adsorption Properties of Silicates Surface-Imprinted with an Organophosphonate" *Langmuir,* 16, 6148-6155 (2000). This approach involves imprinting the shape and functionality of a compound into a metal oxide or polymer matrix. This method generally uses a surfactant-imprint molecule to stamp silica particle surfaces with an imprint molecule as the particles are synthesized within a water-in-oil microemulsion.

The template directed molecular imprinted material may be an organosilica compound such as a polysilsesquioxane prepared from a bis(trialkoxysilyl) organic compound. The general structure of the bis(trialkoxysilyl) organic compound is $(RO)_3Si-R'-Si(OR)_3$ where R is an alkyl group. The R' may be an aryl or alkyl organic bridging group. The material may also be a silica with a pendant organic functional group, such as quaternary ammonium halide, amine, carboxylate, aryl, alkyl, thiol, sulfonate, phosphate, or hydroxyl group. The material may be made from is made from N-trimethoxysilylpropyl-N,N,N-trimethylammonium chloride. The material may be imprinted by an organic molecule or by an organophosphonate or aromatic compound, such as pinacolyl methylphosphonate (PMP). PMP is a stimulant for the nerve agent Soman.

An embodiment of a CASPAR preconcentrator is shown in FIG. 1. The dielectric film may be a polyimide film. The heaters may be platinum heaters. The device may include a sensor coupled to the outlet for detecting vapors. One suitable sensor is an ion mobility sensor. The device may be used by exposing it to an environmental air sample.

The following example is given to illustrate specific applications. These specific example is not intended to limit the scope of the disclosure in this application.

Example

Testing of TMACPTMS-PMP imprinted material—A TDMI organosilica sorbent made from N-trimethoxysilylpropyl-N,N,N-trimethylammonium chloride and imprinted with PMP (TMACPTMS-PMP) was used to coat the CASPAR device. The material may be made as follows, as disclosed by Markowitz et al., *Langmuir,* 16, 6148-6155 (2000). Silica particles are prepared by stirring a mixture of 37 mL of saturated ammonia solution, 25 mL of ethanol, 0.5 g of Igepal CO-520, 13.5 mL of cyclohexane, and 1.44 mL of water for 30 min at room temperature and then adding 3.6 mL of tetraethoxysilane. Imprinted silica particles are prepared by mixing the functionalized silanes and imprinting molecule pinacolyl methylphosphonate in ethanol solution before the addition of tetraethoxysilane. The mixtures are then stirred overnight at room temperature. The resulting dispersions are separated by centrifugation and then washed sequentially with the following solvents: 20 wt % water in ethanol (5×12 mL), acetic acid/ethanol/water (3/3/4, v/v/v) (5×12 mL), 20 wt % water in ethanol (5×12 mL), and ethanol (5×12 mL). The particles are then dried over vacuum for over 10 h at room temperature. With this method, 1 g of silica particles was obtained.

The TMACPTMS-PMP imprinted material was diluted with acetonitrile (anhydrous, 99.8% pure, Aldrich) to make a solution that was 0.93% (by mass) TMACPTMS-PMP imprinted material in acetonitrile. The solution was sonicated for two hours at 30° C. Two hundred and fifty microliters of the solution was drawn into a syringe. The solution was applied drop wise to a CASPAR #93 and allowed to air dry between drops. Some wicking of the solution onto the back of the CASPAR was observed, (CASPAR #93 is a single hotplate not a stacked system. The single hotplate is used for evaluation purposes.) After coating, the CASPAR #93 was placed in a vacuum oven for 1 hour and 30 minutes at 110° C. to remove any residual solvent. It was observed that the entire hotplate was coated except at the very edges. There were areas of thicker coating and areas of thinner coating.

Before placing the CASPAR onto the IMS a clean air flow of approximately 1 L/min was blown through the chip in order to dislodge any possible particulates. After 20 minutes of clean air flow, the CASPAR coated with the TMACPTMS-PMP imprinted material was placed in a custom designed chuck and attached to a Smith's LCD 3.1 handheld IMS detector. A vapor of DMMP (dimethyl methyl phosphonate, a nerve agent stimulant) was generated by bubbling $N_2$ through 30 mL of DMMP at 0° C. and diluted with zero grade air to create a sample concentration of 0.010 mg/m$^3$. The LCD was placed perpendicular to the sample flow so as to assure that the flow through CASPAR would be defined by the detector flow, which was 500 mL/min.

Figure 2:
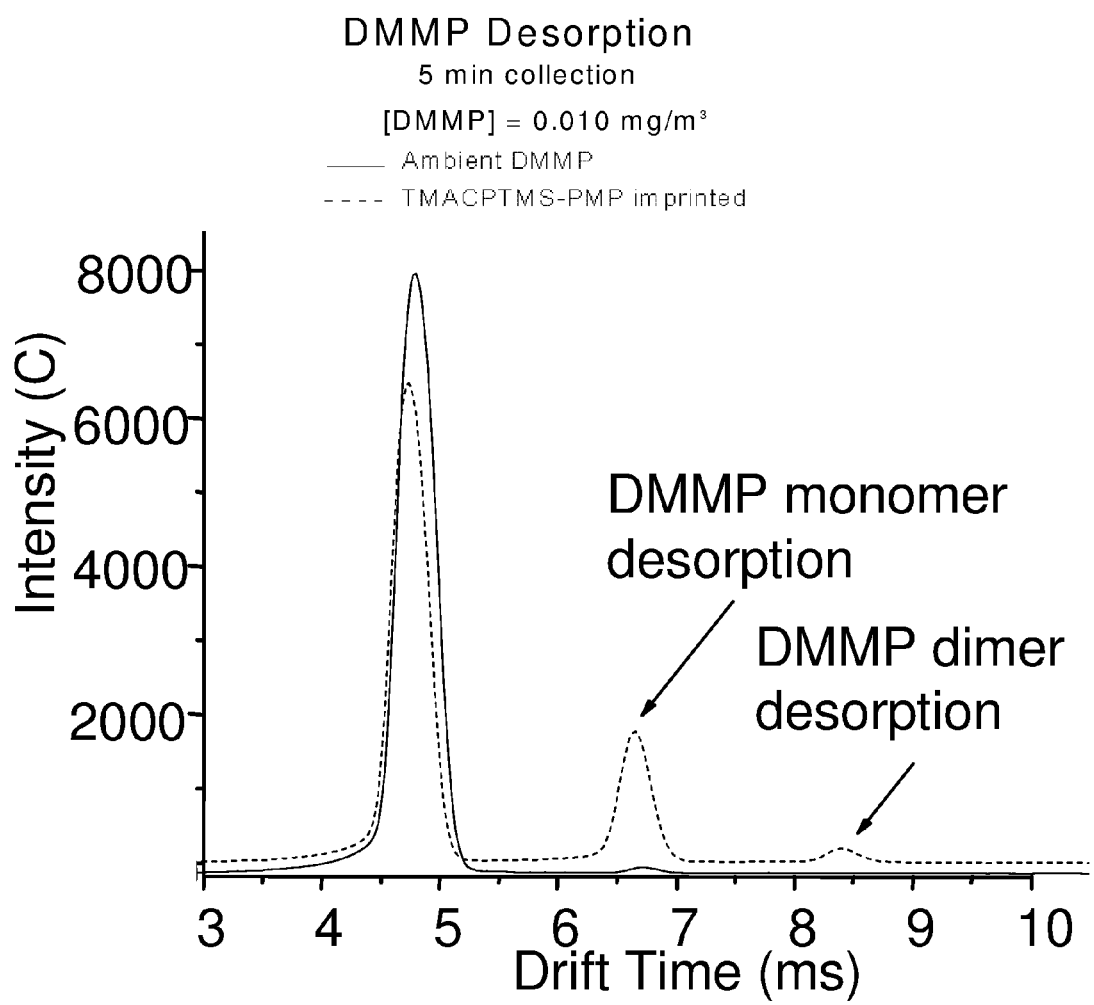
FIG. 2 shows the baseline and TMACPTMS-PMP coated CASPAR response to 0.010 mg/m$^3$ of DMMP using LCD.

A baseline desorption was completed by sampling zero grade dry air for two minutes and then desorbing the CASPAR at 180° C. for three seconds. Once it was confirmed that there was no desorption peak from clean air, 0.010 mg/m$^3$ of DMMP was introduced for five minutes. The average IMS spectra for five trials can be seen in FIG. 2 compared with the IMS response to the ambient 0.010 mg/m$^3$ of DMMP.

The first peak in the graph centered at 4.8 ms is the reactive ion peak. Depression of this peak in the desorption spectra indicates greater signal, as the reactive ion concentration stays constant unless it comes into contact with an analyte. The second and third peak, centered at 6.7 and 8.4 ms respectively, correspond to DMMP. At 0.010 mg/m$^3$ only a small peak can be observed at 6.7 ms also known as the monomer peak. When higher concentrations are present, DMMP molecules will associate in the IMS drift chamber and create a peak at 8.3 ms also known as the DMMP dimer peak. The CASPAR showed significant enhancement of the LCD 3.1 detector response to DMMP when compared with the signal of the LCD 3.1 with no CASPAR.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A device comprising:
   one or more substrates in an enclosure;
   a template directed molecular imprinted material on the substrates;
   an inlet and an outlet of the enclosure that permit air flow through the enclosure and over the substrates; and
   a heater that permits heating the template directed molecular imprinted material.

2. The device of claim 1, further comprising:
   a sensor coupled to the outlet for detecting vapors.

3. The device of claim 2, wherein the sensor is an ion mobility sensor.

4. The device of claim 1, wherein the substrate contains one or more holes that permit air flow through the substrate.

5. The device of claim 1, wherein the substrate is a polyimide film.

6. The device of claim 1, wherein the template directed molecular imprinted material is an organosilica compound.

7. The device of claim 1, wherein the template directed molecular imprinted material is a polysilsesquioxane prepared from a bis(trialkoxysilyl) organic compound.

8. The device of claim 7, wherein the bis(trialkoxysilyl) organic compound has an aryl or alkyl group as an organic bridging group.

9. The device of claim 1, wherein the template directed molecular imprinted material is silica with a pendant functional group.

10. The device of claim 9, wherein the pendant functional group is a quaternary ammonium halide, amine, carboxylate, aryl, alkyl, thiol, sulfonate, phosphate, or hydroxyl group.

11. The device of claim 1, wherein the template directed molecular imprinted material is made from N-trimethoxysilylpropyl-N,N,N-trimethylammonium chloride.

12. The device of claim 1, wherein an organic molecule is used as an imprint molecule to form the template directed molecular imprinted material.

13. The device of claim 1, wherein an organophosphonate or aromatic compound is used as an imprint molecule to form the template directed molecular imprinted material.

14. The device of claim 1, wherein pinacolyl methylphosphonate is used as an imprint molecule to form the template directed molecular imprinted material.

15. The device of claim 1, wherein the heater is one or more platinum heaters on the substrate.

16. A method comprising:
    providing a device comprising:
      one or more substrates in an enclosure;
      a template directed molecular imprinted material on the substrates;
      an inlet and an outlet of the enclosure that permit air flow through the enclosure and over the substrates;
      a heater that permits heating the template directed molecular imprinted material; and
      a sensor coupled to the outlet for detecting vapors;
    flowing a gas though the device during a sampling period;
    heating the template directed molecular imprinted material with the heater after the sampling period; and
    flowing any vapor evolved from the template directed molecular imprinted material during the heating into the sensor.

17. The method of claim 16, wherein the gas is an environmental air sample.

18. The method of claim 16, wherein the sensor is an ion mobility sensor.

19. The method of claim 16, wherein the substrate contains one or more holes that permit air flow through the substrate.

20. The method of claim 16, wherein the substrate is a polyimide film.

21. The method of claim 16, wherein the template directed molecular imprinted material is an organosilica compound.

22. The method of claim 16, wherein an organophosphonate or aromatic compound is used as an imprint molecule to form the template directed molecular imprinted material.

23. The method of claim 16, wherein pinacolyl methylphosphonate is used as an imprint molecule to form the template directed molecular imprinted material.

24. The method of claim 16, wherein the heater is one or more platinum heaters on the substrate.

* * * * *